United States Patent
Langer et al.

(10) Patent No.: US 7,335,880 B2
(45) Date of Patent: Feb. 26, 2008

(54) TECHNIQUE FOR CD MEASUREMENT ON THE BASIS OF AREA FRACTION DETERMINATION

(75) Inventors: Eckhard Langer, Radebeul (DE); Moritz-Andreas Meyer, Dresden (DE)

(73) Assignee: Advanced Micro Devices, Inc., Austin, TX (US)

( * ) Notice: Subject to any disclaimer, the term of this patent is extended or adjusted under 35 U.S.C. 154(b) by 316 days.

(21) Appl. No.: 11/281,169

(22) Filed: Nov. 17, 2005

(65) Prior Publication Data

US 2006/0219906 A1 Oct. 5, 2006

(30) Foreign Application Priority Data

Mar. 31, 2005 (DE) .................. 10 2005 014 793

(51) Int. Cl.
*H01J 37/28* (2006.01)
(52) U.S. Cl. .................. 250/310; 250/306; 250/307; 250/311
(58) Field of Classification Search .......... 250/306, 250/307, 310, 311
See application file for complete search history.

(56) References Cited

U.S. PATENT DOCUMENTS

| | | | |
|---|---|---|---|
| 6,252,412 B1 * | 6/2001 | Talbot et al. ............... | 324/750 |
| 6,368,879 B1 * | 4/2002 | Toprac ............................ | 438/5 |
| 7,253,909 B1 * | 8/2007 | Li et al. ...................... | 356/625 |
| 2002/0113234 A1 | 8/2002 | Okuda et al. ................. | 257/48 |
| 2002/0117635 A1 | 8/2002 | Shinada et al. ........... | 250/492.3 |
| 2003/0089851 A1 | 5/2003 | Katagami et al. ........... | 250/307 |
| 2003/0201391 A1 | 10/2003 | Shinada et al. ............. | 250/307 |
| 2003/0206027 A1 | 11/2003 | Nozoe et al. ............... | 324/751 |

FOREIGN PATENT DOCUMENTS

JP 2000276592 A 10/2000

* cited by examiner

*Primary Examiner*—Jack I. Berman
*Assistant Examiner*—Michael J Logie
(74) *Attorney, Agent, or Firm*—Williams, Morgan & Amerson, P.C.

(57) ABSTRACT

The present invention provides a technique for estimating critical dimensions of highly scaled circuit features on the basis of scanning electron microscopy, wherein area fractions of a scan area are determined. Preferably, the SEM is operated with high electron beam energies to enhance the overall resolution and to reduce edge effects and image artifacts. Thus, fast and statistically significant measurement results may be obtained, thereby allowing enhanced process control.

11 Claims, 3 Drawing Sheets

TECHNIQUE FOR CD MEASUREMENT ON THE BASIS OF AREA FRACTION DETERMINATION

BACKGROUND OF THE INVENTION

1. Field of the Invention

Generally, the present invention relates to metrology in the manufacturing of microstructures, such as integrated circuits, and, more particularly, to the measurement and monitoring of the dimensions of microstructure features by means of metrology tools, such as a scanning electron microscope (SEM).

2. Description of the Related Art

In manufacturing microstructures, such as integrated circuits, micromechanical devices, opto-electronic components and the like, device features such as circuit elements are typically formed on an appropriate substrate by patterning the surface portions of one or more material layers previously formed on the substrate. Since the dimensions, i.e., the length, width and height of individual features, are steadily decreasing to enhance performance and improve cost-effectiveness, these dimensions have to be maintained within tightly set tolerances in order to guarantee the required functionality of the complete device. Usually a large number of process steps have to be carried out for completing a microstructure, and thus the dimensions of the features during the various manufacturing stages have to be thoroughly monitored to maintain process quality and to avoid further cost-intensive process steps owing to process tools that fail to meet the specifications in an early manufacturing stage. For example, in highly sophisticated CMOS devices, the gate electrode, which may be considered as a polysilicon line formed on a thin gate insulation layer, is an extremely critical feature of a field effect transistor and significantly influences the characteristics thereof. Consequently, the size and shape of the gate electrode has to be precisely controlled to provide the required transistor properties. Thus, great efforts are being made to steadily monitor the dimensions of the gate electrode.

Device features are commonly formed by transferring a specified pattern from a photomask or reticle onto a radiation-sensitive photoresist material by optical imaging systems with subsequent sophisticated resist treating and development procedures to obtain a resist mask having dimensions significantly less than the optical resolution of the imaging system. It is therefore of great importance to precisely control and monitor the dimensions of these resist features, as these features that determine the dimensions of the actual device features may be "reworked" upon detecting a deviation from the process specification.

A frequently used metrology tool for determining feature sizes in a non-destructive manner is the scanning electron microscope (SEM), which is able, due to the short wavelength of the electrons, to resolve device features having dimensions, also referred to as critical dimensions (CD), in the deep sub-micron range. Basically, in using an SEM, electrons emitted from an electron source are focused onto a small spot of the substrate via a beam shaping system. Secondary radiation generated by the incident electrons is then detected and appropriately processed and displayed. Although an SEM exhibits a superior resolution compared to optical measurement tools, the accuracy of the measurement results strongly depends on the capability of correctly adjusting the focus of the SEM, i.e., appropriately adjusting one or more tool parameters, such as the lens current of a magnetic lens, the acceleration voltage of the incident electron beam, and the like. For instance, in scanning a device feature such as a line, an electron beam that is not set to the optimized focus condition may result in an increased measurement value, whereas scanning a trench with a slightly defocused electron beam may lead to an underestimation of the actual trench width. Since the ever-decreasing features sizes of sophisticated microstructures pose very strict constraints on the controllability of critical dimensions, the measurement tolerances of the metrology tools become even more restricted as the tightly set critical dimensions have to be monitored in a reproducible and reliable manner.

In view of the problems outlined above, SEM tools have been recently introduced that are adapted to carry out dimension measurements in a substantially completely automatic manner. That is, these SEM tools repeat for each measurement target a process sequence including pattern recognition, automatically focusing the tool and measuring the pattern under consideration. With shrinking features sizes, however, automatically determining optimum resolution conditions and subsequently determining reliable measurement results by image analysis routines becomes more and more challenging as, for example, the beam shaping system of modern SEM tools is designed to give an optimum resolution with lower and lower focus depth, while at the same time features with steadily reduced sizes produce less signal for the automated focus and image analysis algorithms implemented in these tools. Consequently, if any routine for determining an optimum resolution of an inspection tool is carried out, the obtained setting may include a certain degree of uncertainty that is determined by the specific inspection tool used and the operational behavior, for example the implemented focus-finding and image analysis algorithms, and the current conditions thereof, as the resolution depends on a variety of parameters, such as condenser lens current, stigmatism, working distance, accelerating voltage, and the like.

Thus, although modern state of the art inspection tools allow improved precision and throughput by automatic determination of appropriate focus and resolution conditions in combination with image analysis, the demand for tightly set measurement tolerances required for features sizes of 0.08 nm and even less may not be satisfactorily met by presently available inspection tools. For example, conventional SEM devices may generate CD measurement data on the basis of edges automatically identified in the image, since, due to the so-called edge effect, the emission of secondary electrons is enhanced when the focused electron beam encounters during its scanning movement a protrusion, such as the sidewall of a line feature. The increased release of secondary electrons results in a bright spot on the displayed image due to the increased current produced by the secondary electron detector. Typically, for measuring critical dimensions in resist features and etched features of advanced semiconductor devices, electron energies of several hundred volts up to approximately 2000-3000 volts are used to release electrons close to the sample surface for providing a high contrast caused by edges of the sampled feature, such as a resist line. By determining edges in the image produced by the secondary electron detector, a corresponding distance and thus CD of the feature may be estimated. However, the assessment of the detector image by automated image analysis algorithms strongly depends on the SEM settings, as is previously explained. Moreover, the pronounced edge effect may also give rise to image artifacts, thereby resulting in incorrect CD estimates. The situation may even become worse for advanced devices, such as gate electrode structures of the 90 nm technology and less, since here typically highly sensitive resists may be used which suffer from an increased sensitivity to interaction with the incident electron beam, thereby further contributing to, in addition to image artifacts, a reduced overall resolution. Increasing the number of measurement runs per feature in order to improve measurement accuracy may be less desirable due to an increase of measuring time and higher complexity for evaluation algorithms, as these algorithms may have to account for corrections with respect to the increased interaction.

In view of the above problems, there exists a need for a technique that enables the determination and monitoring of dimensions of features in the deep sub-micron regime with a minimal variation and high statistical significance.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present invention is directed to a technique for estimating and/or monitoring critical dimensions of features during the fabrication of these features, wherein high statistical significance of measurement results is obtained for an image of a selected area including these features, in that an area fraction is determined rather than determining a distance on the basis of pronounced edges identified in the image as in conventional SEM techniques.

According to one illustrative embodiment of the present invention, a method of monitoring critical dimensions of features formed on a substrate is provided. The method comprises scanning an area of the substrate by a scanning inspection tool to obtain an image of the area, wherein the area includes at least a portion of one or more of the features. Furthermore, an area fraction in the image is determined on the basis of at least one image parameter and a predefined threshold for the parameter. Finally, the area fraction is used as a measure of a mean value of the critical dimension in the area.

According to a further illustrative embodiment of the present invention, an inspection system comprises a measurement section configured to generate an image signal in response to scanning a selected area of a surface portion of a substrate. Moreover, an image processing section is provided and is configured to establish an image of the selected area on the basis of the image signal. The system further comprises an area calculation section configured to determine an area fraction in the image on the basis of a threshold for a predefined image parameter. Additionally, the system comprises a comparison unit configured to compare the area fraction with a reference value for estimating critical dimensions of features contained in the area.

BRIEF DESCRIPTION OF THE DRAWINGS

The invention may be understood by reference to the following description taken in conjunction with the accompanying drawings, in which like reference numerals identify like elements, and in which.

Figure 1A:
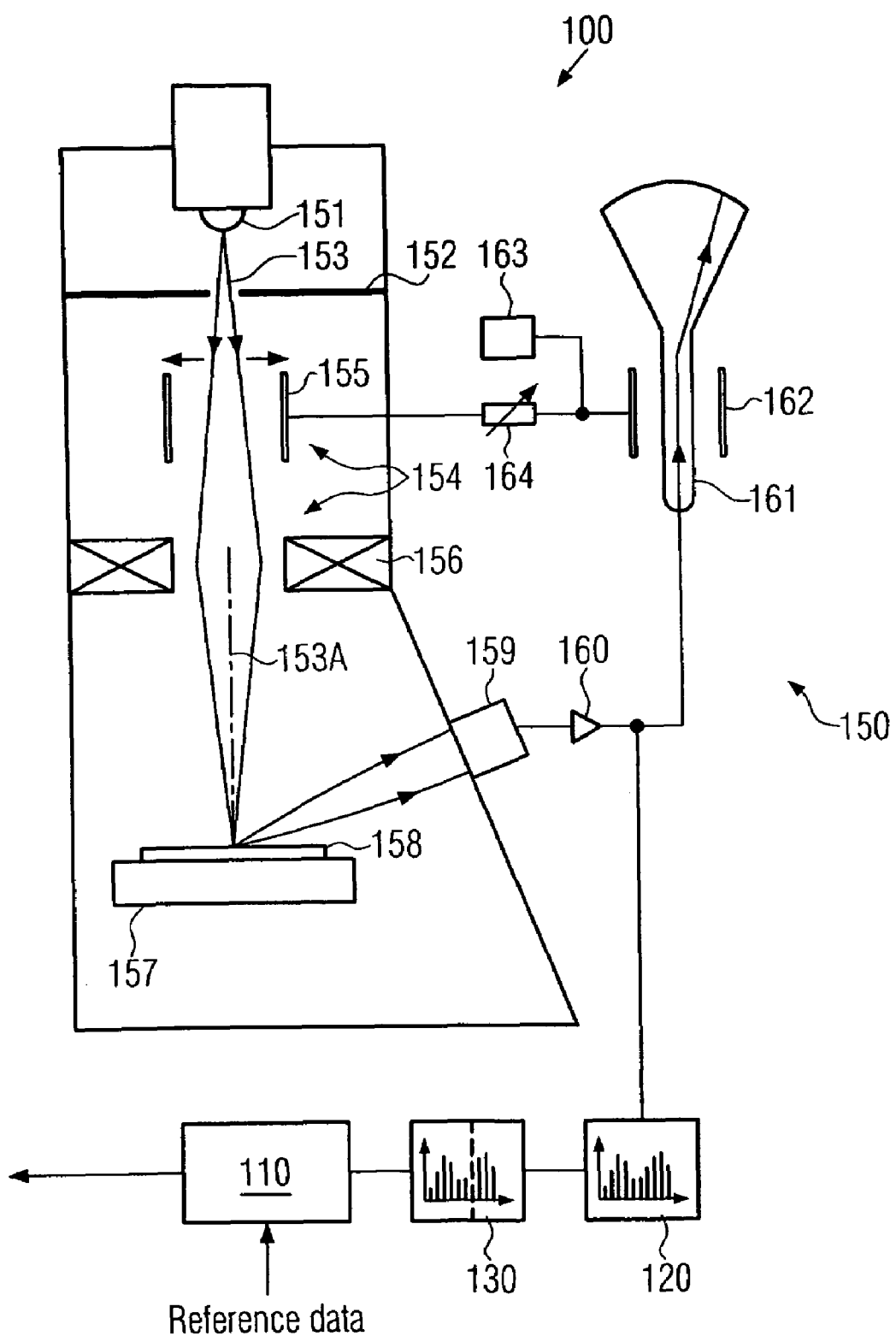
FIG. 1a schematically depicts an inspection system including an SEM, a calculation section and an area fraction comparison section in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

As previously noted, decreasing feature sizes and economic demands require manufacturers of microstructures to employ metrology systems for CD measurement and monitoring, ensuring accurate measurement results while providing a high throughput. Automated metrology tools for non-destructive CD measurements may represent extremely complex and expensive tools in a process line, wherein the required process margins are nevertheless very difficult to be met, especially when taking future device generations into consideration, which may have gate lengths of 50 nm and even less. Since the gate patterning process with its extremely complex lithography process is an essential step in manufacturing advanced semiconductor devices, it is of great importance to provide highly efficient but nevertheless accurate measurement processes for monitoring the quality of the gate patterning process.

As the lithography process is performed step-wise, i.e., on the basis of a plurality of exposure fields, the across-substrate uniformity may be controlled by correspondingly selecting exposure parameters for the individual exposure steps. Moreover, since the exposure process may be repeated upon detection of exposures failures, it is highly desirable to obtain measurement data from resist features with high accuracy and high statistical relevance to allow a fast response to local fluctuations. The present invention therefore provides a technique based on a scanning metrology tool, such as an SEM, wherein image data obtained from a selected area are evaluated on the basis of pixel data related to area-like image characteristics rather than attempting to identify pronounced image features, such as edges of line features, and calculating a representative distance. Thus, a fast and precise measure of a mean value of critical dimensions may be obtained, which may readily be compared to reference values, such as corresponding measures for mean values of areas in other die regions of the same substrate. Moreover, the efficiency of the area fraction determination may be enhanced in that the tool parameters of the SEM may be set to reduce image artifacts and enhance the overall resolution.

Thus, in some particular embodiments, the electron beam acceleration voltage may significantly be increased compared to conventional techniques of measuring critical dimensions of semiconductor devices. Accordingly, the edge effect, and therefore the creation of image artifacts that may be associated therewith, may be reduced, while also the overall resolution of the SEM tends to improve at these higher electron energies for typical materials of semiconductor features.

With reference to FIG. 1a-1d, an inspection system and a method for non-destructive CD measurement and/or monitoring in accordance with illustrative embodiments of the present invention will now be described.

In FIG. 1a, an inspection system 100 comprises a measurement section 150, an image processing section 120, an area calculation section 130 and a comparison section 110. The measurement section 150 includes a cathode 151 and an anode 152, which are configured and arranged to produce, in operation, an electron beam 153. A beam shaping system 154 includes deflecting elements 155, for example provided in the form of electrode plates and/or solenoids, and one or more magnetic lenses 156. A support 157 is adapted and arranged to hold a substrate 158, for example a semiconductor substrate including features of critical dimensions of approximately 50 nm and less. For convenience, any means required for loading and unloading the substrate 158 onto the support 157 are not shown. A detector 159, such as a Faraday cup, coupled to an amplifier 160 is positioned to receive a signal from the substrate 158. Display means 161, such as a cathode ray tube (CRT), is coupled to the amplifier 160 and is further adapted to produce a signal indicative of the signal received by the detector 159 via the amplifier 160. In the case of the CRT 161, deflecting elements 162 may be provided that are coupled via a magnification adjustment element 164 to the beam deflecting elements 155. Moreover, a scan generator 163 is connected to the deflecting elements 155 and 162. It should be noted, however, that the display means 161 is to represent any appropriate arrangement that allows monitoring and/or recording of an output signal provided by the amplifier 160.

During operation of the inspection system 100, the substrate 158 is loaded onto the support 157 and the measurement section 150 is evacuated to establish appropriate environmental conditions for generating the electron beam 153. Thereafter, a typical pattern, which will be described with reference to FIG. 1b, and which includes one or more features to be inspected, is identified by, for example, optical means (not shown) or by appropriately adjusting the magnification system 164 to obtain a relatively wide view of the substrate 158, allowing the recognition of the pattern of interest. It should be noted that, for example, suitable image processing means may be provided when optical means are used for identifying the pattern of interest. When the electron beam 153 is used for identifying the target pattern, the tool parameters, such as magnification, acceleration voltage of the beam 153 and the like, may appropriately be set to obtain an appropriate signal from the detector 159 and the amplifier 160, which is suitable for the pattern recognition by means of the image processing section 120. For instance, an acceleration voltage applied between the cathode 151 and the anode 152 and/or a current supplied to the one or more magnetic lenses 156 may be selected in accordance with predefined default values to produce image signals allowing the identification of the target pattern.

Once the target pattern is identified, the tool parameters are set to establish the focus condition for the actual measurement process, wherein these parameters may be provided in advance or may be determined on the basis of automated focus algorithms and the like. In a particular embodiment, the beam acceleration voltage is adjusted to a range of approximately 5 kV (kilovolt) or higher, or may be set in one illustrative embodiment to approximately 10 kV or more. Moreover, the substrate 158 is oriented with respect to the electron beam 153, i.e., with respect to a beam axis 153a, such that the beam axis 153a is substantially perpendicular to the surface of the substrate 158. The term "substantially perpendicular" in this respect describes an angle between the surface of the substrate 158 and the beam axis 153a, which may be in the range of approximately 87-93 degrees. The electrons of the beam 153 impinging on the substrate 158 create a plurality of secondary signals, such as secondary electrons released from the substrate material, electrons scattered by the substrate material, x-rays created by the absorption of primary electrons and/or the emission of secondary electrons, and the like. At least one of these signals is detected by the detector 159, wherein, in typical SEM applications, primarily the secondary electrons are detected. The corresponding signal output by the detector 159 and amplified by the amplifier 160 is supplied to the image processing section 120, which may store the output signals to thereby establish an image of the area of interest after completion of the scan operation.

Figure 1B:
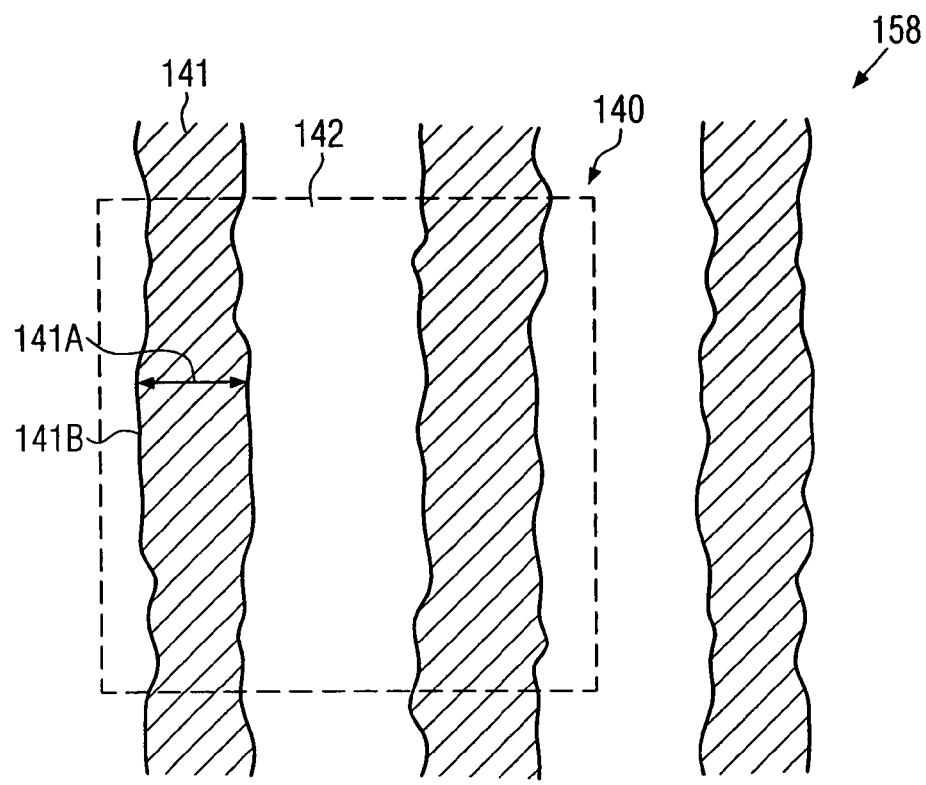
FIG. 1b schematically illustrates in a plan view a portion of a test structure including a plurality of line-like features, which is scanned by an electron beam according to illustrative embodiments of the present invention.

FIG. 1b schematically shows a plan view of a portion of the substrate 158. The portion shown may represent a test structure formed on a specified location on the substrate 158. As previously noted, the test structure of interest may include appropriate patterns to allow the identification of the test structure and to position the substrate 158 relative to the electron beam 153 to define a scan area 140, the dimensions of which are substantially determined by the specific tool parameters used for the subsequent measurement process. The scan area 140 may include at least a portion of one or more features 141 and 142, which may be configured as lines and spaces, wherein the features 141 may represent line-like features formed on and protruding above an underlying material layer, which may represent the space "feature" 142. In a particular embodiment, the features 141, 142 may be formed in a common manufacturing process carried out for forming corresponding features or circuit elements in other substrate regions. For example, the features 141 may represent resist features, hard mask features, actual gate electrode features and the like, as are substantially identically formed in product areas of the substrate 158. Consequently, the features 141 may be viable representatives of the actual circuit features for which corresponding critical dimensions, such as a length 141a, may be monitored, as this length 141a may significantly affect the overall performance of actual circuit elements formed on the substrate 158.

As previously noted, highly complex lithography processes are involved in manufacturing the features 141 so that the length 141a may vary in accordance with process non-uniformities. For example, for highly scaled semiconductor devices, a gate length, i.e., the length 141a, may vary within a single structure or may vary from line element to line element. For this reason, determining a representative length, such as length 141a, along a single path across one of the features 141 may result in a moderately high variance of the corresponding value, thereby rendering these results as less efficient in the control of the manufacturing process. Moreover, conventional techniques attempting to precisely measure the length 141a rely on an efficient recognition of edges 141b by appropriately designed edge recognition algorithms. As previously explained, by scanning an electron beam of a conventional SEM system across the features 141, a significant increase of the generation of secondary electrons may occur at the edges 141b, thereby providing a high contrast in the image of the scan area 140. However, although a significant contrast enhancement may be obtained, the edge effect also may give rise to image artifacts, which in turn, may result in incorrectly detected edges and thus in an incorrectly calculated dimension 141a.

Contrary to conventional approaches, the present invention uses the image data of the scan area 140 and extracts a two dimensional measure, such as an area fraction occupied by, for example, the features 141 within the scan area 140. In other examples, the fraction of pixels considered to belong to the feature 141 may be related to the pixels considered to belong to the spaces 142. Since a measure for the critical dimension 141a is obtained on the basis of an area fraction or area ratio, a statistically significant mean value is obtained, while the variance thereof is less pronounced compared to averaging a plurality of actually measured distances 141a, since the determination of the corresponding area or area fraction may be based on a single threshold rather than a plurality of edge positions to be determined, thereby reducing any errors that may be obtained when individually determining the location of the edges 141b, in particular when image artifacts are present. Furthermore, the determination of a measure for the particular dimension 141a on the basis of a ratio or area fraction makes the procedure more insensitive to tool parameter variations, since any effects influencing the tool resolution may equally concern the lines 141 and the spaces 142 in the image of the scan area 140. Although the determination of an absolute mean value for the length 141a may require the provision of appropriate reference data, nevertheless significant data may be obtained to enable a meaningful comparison between data gathered from different scan areas 140 across the substrate 158 or from different substrates 158 while a sensitivity to tool variations, algorithm-induced errors and image artifacts is reduced.

Moreover, in particular embodiments, the electron beam energy is selected to be approximately 5 kV and higher, or even 10 kV or higher, so that, compared to conventional SEM systems, the spherical aberration of the measurement section 150 may be reduced, thereby increasing the overall resolution of the inspection system 100. In addition, the increased accelerating voltage may increase the secondary yield from all parts of the features 141 and 142 due to a greater beam penetration. Consequently, the edge effect, that is the contrast enhancement at the edges 141b, may be reduced and thus may have a diminishing effect on the contrast, thereby also reducing the probability for creating image artifacts. Therefore, in these embodiments, an enhanced resolution in combination with a reduced number of image artifacts may further improve the accuracy in determining an appropriate area fraction within the scan area 140.

Figure 1C:
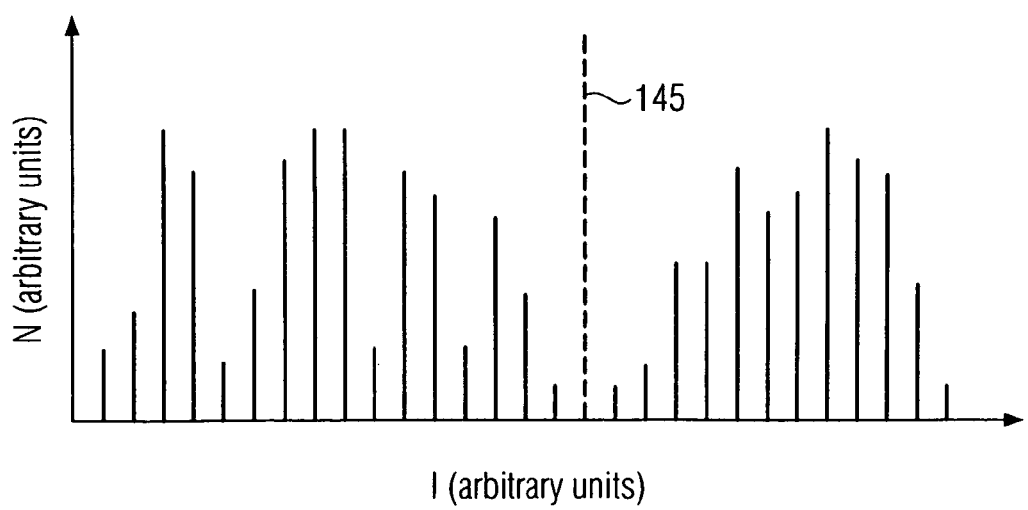
FIG. 1c is an exemplary graph illustrating a typical result of an intensity distribution for determining an area fraction on the basis of a threshold value for the intensity.

FIG. 1c schematically depicts an exemplary representation of image data that may be obtained by the image processing section 120 after completion of the scan operation of the scan area 140. In FIG. 1c, the horizontal axis may represent an appropriate image parameter for determining an area fraction within the area 140. In one embodiment, the image parameter may represent the pixel value or the combination of a plurality of pixel values of the image of the scan area 140. That is, for each position during the scanning of the electron beam 153 across the scan area 140, the corresponding signal intensity provided by the amplifier 160 may correspond to an intensity value of the corresponding pixel in the image of the scan area 140. For example, the pixel value may represent a grey scale of the image of the scan area 140. By using a moderately high electron beam energy, as previously explained, the edge effects and thus the contrast enhancement are significantly reduced, thereby also reducing the required "dynamic" range for the pixel values that may occur during the entire scan operation. As a consequence, less pronounced density variations created, for instance, by the protruding features 141 compared to the lower lying spaces 142 may be resolved more efficiently, due to the lack of contrast peaks that would result in conventional techniques at low beam energies.

The vertical axis in FIG. 1c may represent the number of pixels or pixel groups belonging to a specified intensity value. Since the total number N of pixel elements or pixel groups is determined by the scan area 140, the total number represents a measure of the total area of the scan area 140. Consequently, the area fraction may be determined with reference to this total area or may be determined as a ratio of individual portions within the scan area 140.

After generating the image data by the image processing section 120, which may include any further procedures, such as noise reduction, appropriate smoothing of the histogram and the like, the data may be supplied to the area fraction calculating section 130, in which an appropriate area or area fraction may be determined on the basis of the image data. In one illustrative embodiment, a threshold or threshold range may be defined in order to delimit, for instance, an area considered to belong to the feature 141 from an area considered to belong to the feature 142. As previously explained, the response to the scanning electron beam 153 moved across the various features 141 and 142 may differ in that the feature 142 may typically generate less secondary electrons, thereby producing image data of less intensity compared to image data produced by the features 141. For example, a threshold 145 may be determined to "identify" pixels belonging to the feature 141, i.e., pixels above the threshold 145, and pixels belonging to the feature 142, i.e., pixels below the threshold 145. Based on the threshold 145, the corresponding number of pixel or pixel groups may be used to calculate an area, i.e., in FIG. 1c, the value N for all intensities above the threshold 145 may be added to obtain a measure for the area corresponding to the feature 141, while a corresponding number of pixel or pixel groups having intensities below the threshold 145 may be added to obtain a measure of an area corresponding to the feature 142. Since the number of pixels or pixel groups corresponds to the number of scan steps or at least is correlated thereto, the respective sums above and below the threshold 145 present a direct measure of the corresponding areas. The threshold 145 may be estimated for each scan operation on the basis of predefined criteria, or the threshold 145 may be determined for a plurality of measurement operations, for instance, for measuring a plurality of measurement sites on the substrate 158 or on a plurality of substrates 158.

For example, the threshold 145 may be selected on the basis of a predefined pattern recognition of the image data, for instance by identifying data clusters at higher intensities as is for instance shown in FIG. 1c or the threshold value 145 may be selected in accordance with a maximum intensity obtained during scanning of the area 140. That is, the "dynamic" range obtained for scanning different areas 140 may vary, wherein the threshold may be selected on the basis of the obtained range so that the position of the threshold may be scaled in accordance with the variation of the dynamic range. In other embodiments, a plurality of reference data may have been analyzed to establish an appropriate position of the threshold 145 on the intensity axis. Moreover, analyzing of any reference image data, such as the histogram shown in FIG. 1c, may provide further criteria for smoothing or otherwise manipulating the image data prior to establishing an appropriate threshold value. For example, criteria for identifying any outliners may be established so as to exclude certain intensity values or value ranges. It should be appreciated that, upon selection of appropriate criteria for establishing the threshold value 145, the result of the calculation of an area fraction for a plurality of measurement runs is moderately insensitive to the exact location of the threshold 145, as its position may also be affected by the same variations of the measurement procedure as are the image data.

After the calculation of an area fraction, for instance the ratio of the number of pixels above the threshold 145 and the number of pixels below the threshold 145, the corresponding result may be supplied to the comparison section 110, which may be configured to use the area fraction as a measure of the critical dimension under consideration, such as a mean value for the length 141a. For example, the comparison section 110 may have implemented therein a reference data to allow the estimation of the currently obtained measure for the length 141a with respect to the reference data. Consequently, a drift or significant variation of the currently obtained area fraction from the reference data may be indicated to an operator or to a supervising control system to enable the control of preceding or subsequent processes on the basis of the identified deviation. In illustrative embodiments, the measurement data, i.e., the area fractions determined as described above, may be stored and/or may be used to update the reference data, thereby allowing an enhanced process control, since substrate-to-substrate variations and also across-substrate variations may readily be detected.

Figure 1D:
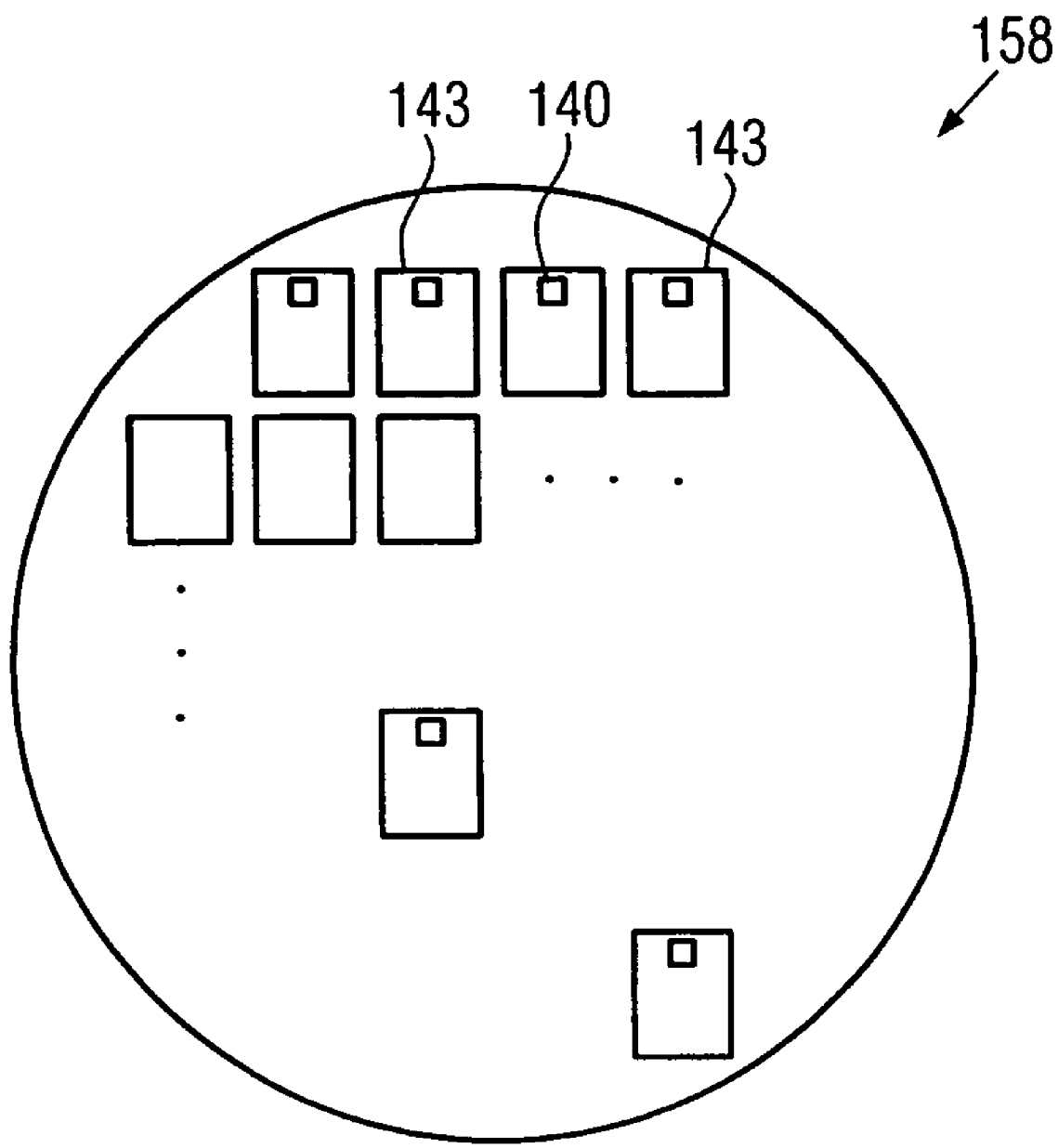
FIG. 1d schematically depicts a plurality of die regions on a substrate for obtaining a plurality of area fractions for estimating across-substrate process non-uniformity.

FIG. 1d schematically shows the substrate 158 in a plan view, wherein a plurality of die regions 143 are formed on the substrate 158. Each of the die regions 143 may comprise a test structure, which may be used in a measurement sequence as described above to establish respective scan areas 140. Thus, all or some of the die regions 143 may be subjected to a measurement procedure as described above to determine respective area fractions and thus measures for corresponding critical dimensions, which may be compared with each other to estimate the across-substrate uniformity of the critical dimensions and thus of the processes involved in forming the respective features in the scan area 140. Since the determination of the area fractions is performed in a fast and statistically relevant manner, as the sensitivity to tool and measurement process variations and image artifacts is reduced, a plurality of die regions 143 may be measured, even for large-diameter substrates, thereby providing the potential for increasing the efficiency of any advanced process control (APC) systems and strategies involved in the manufacturing processes. For example, since a moderately high number of die regions 143 may be subjected to a measurement process for estimating a mean value of a critical dimension, a moderately high resolution for providing measurement data for a respective exposure map of a lithography process may be accomplished.

As a result, the present invention provides an improved technique for estimating a mean value of critical dimensions. even of highly scaled circuit elements, such as gate electrodes having a gate length of approximately 50 nm and even less, by scanning electron microscopy, wherein area fractions of a scan area are determined and are used as measure for a critical dimension. Preferably, the SEM is operated at moderately high electron energies to reduce image artifacts and increase the overall resolution of the microscope. Consequently, a measure of the critical dimension may be obtained in a highly efficient manner with increased statistical relevance, since the area fraction may exhibit a reduced sensitivity to tool variations and image processing algorithms. The obtained area fractions are thus highly advantageous in comparing respective measurements to detect process variations. Thus, resist features used in producing gate electrodes or hard features, e.g., the gate electrodes themselves, may efficiently be monitored in view of various manufacturing process variations. For enhancing the control efficiency, the area fraction data may also be correlated to other measurement data, such as TEM (transmission electron microscope) data, SEM data of actually determined dimensions, scatterometry data, electrical performance data and the like, to provide a "reference" for obtaining "absolute" measures for the critical dimensions on the basis of the area fraction data. For instance, the influence of any threshold finding algorithms on the significance of the area fraction data may be estimated to facilitate the selection of appropriate selection criteria. Consequently, highly accurate measurements may be performed, which enable the monitoring of the process quality on a substrate-to-substrate basis as well as on a die-to-die basis.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of monitoring critical dimensions of features formed above a substrate, the method comprising:
   scanning an area of said substrate by a scanning inspection tool to obtain an image of said area, said area including at least a portion of one or more of said features;
   determining an area fraction in said image on the basis of at least one image parameter and a predefined threshold for said parameter; and
   using said area fraction as a measure of a mean value of said critical dimension in said area.

2. The method of claim 1, wherein said inspection tool comprises a scanning electron microscope (SEM).

3. The method of claim 2, wherein scanning said area comprises directing a beam of primary electrons onto a surface comprising said area, said beam defining a beam axis, wherein said beam axis is oriented substantially perpendicular to said surface.

4. The method of claim 2, wherein scanning said area comprises directing a beam of primary electrons onto a surface comprising said area and wherein an acceleration voltage of said primary electrons is approximately 5 kV or more.

5. The method of claim 4, wherein said acceleration voltage is approximately 10 kV or more.

6. The method of claim 1, further comprising:
   selecting a second area on said substrate;
   scanning said second area by said scanning inspection tool to obtain an image of said second area, said second area including at least a portion of one or more of said features;
   determining a second area fraction in said image of the second area on the basis of at least one image parameter and said predefined threshold for said parameter; and
   using said second area fraction and said area fraction for evaluating uniformity of said features across said substrate.

7. The method of claim 1, wherein said image parameter represents an intensity value of pixels of said image.

8. The method of claim 1, wherein said area is a portion of a test structure in a die region of a semiconductor device.

9. The method of claim 8, wherein said features represent line-like features that are formed in a common manufacturing process for forming gate electrode structures.

10. An inspection system, comprising:
    a measurement section configured to generate an image signal in response to scanning a selected area of a surface portion of a substrate;
    an image processing section configured to establish an image of said selected area on the basis of said image signal;
    an area calculation section configured to determine an area fraction in said image on the basis of a threshold for a predefined image parameter; and
    a comparison unit configured to compare said area fraction with a reference value for estimating critical dimensions of features contained in said area.

11. The inspection tool of claim 10, wherein said measurement section comprises a scanning electron microscope.

* * * * *